United States Patent [19]

Siegemund et al.

[11] 4,088,701
[45] May 9, 1978

[54] 1,2,2,2-TETRAFLUOROETHYL-FLUOROMETHYL ETHER AND PROCESS FOR PREPARING IT

[75] Inventors: Günter Siegemund, Hofheim, Taunus; Roman Muschaweck, Frankfurt am Main, both of Germany

[73] Assignee: Hoechst Aktiengesellschaft, Frankfurt am Main, Germany

[21] Appl. No.: 684,489

[22] Filed: May 10, 1976

[30] Foreign Application Priority Data

May 12, 1975 Germany ........................... 2520962

[51] Int. Cl.$^2$ ...................... C07C 43/00; C07C 43/12; A61K 31/08
[52] U.S. Cl. .................................. 260/614 F; 424/342
[58] Field of Search ........................................ 260/614 F

[56] References Cited

U.S. PATENT DOCUMENTS

| 3,637,477 | 1/1972 | Croix | 260/614 F X |
| 3,862,241 | 1/1975 | Terrell | 260/614 F |

FOREIGN PATENT DOCUMENTS

| 2,361,058 | 6/1975 | Germany | 260/614 X |

OTHER PUBLICATIONS

Siegemund, Ber. 106, No. 9 (1973) pp. 2960–2968.
Terrell et al., J. Med. Chem. 15, 604–606, 1972.
Brandwood et al., Chem. Abs. 83, 78488y, 1975, J. Fluorine Chem. (1975), 5(6) 521–535.

*Primary Examiner*—Howard T. Mars
*Attorney, Agent, or Firm*—Curtis, Morris & Safford

[57] ABSTRACT

The invention relates to 1,2,2,2-tetrafluoroethyl-fluoromethyl ether, to a process for preparing it and to its use as inhalation anesthetic.

1 Claim, No Drawings

1,2,2,2-TETRAFLUOROETHYL-FLUOROMETHYL ETHER AND PROCESS FOR PREPARING IT

The present invention relates to the 1,2,2,2-tetrafluoroethyl-fluoromethyl ether of the formula $$CF_3-CHF-O-CH_2F \qquad I$$

and to a process for preparing it, which comprises subjecting a 1,2,2,2-tetrahalogenoethyl-methyl ether of the formula $$CF_{3-n}Cl_nCHF_{1-m}Cl_m-O-CH_3 \qquad II$$

in which $n$ is 0 to 3 and $m$ is 0 or 1, to a partial photochlorination under formation of the 1,2,2,2-tetrahalogenoethyl-chloromethyl ether of the general formula $$CF_{3-n}Cl_nCHF_{1-m}Cl_m-O-CH_2Cl \qquad III$$

in which $n$ and $m$ have the meanings given for formula II, fluorinating the compound obtained of the formula III and isolating the ether obtained from the fluorination mixture by conventional methods.

The invention furthermore provides inhalation anesthetics which contain 1,2,2,2-tetrafluoroethyl-fluoroethyl-fluoromethyl ether and the use of 1,2,2,2-tetrafluoroethyl-fluoromethyl ether as inhalation anesthetic.

The process for preparing the 1,2,2,2-tetrafluoroethyl-fluoromethyl ether of the formula (I) comprises stepwise selective chlorinations and fluorinations of the starting compounds $CF_{3-n}Cl_n-CHF_{1-m}Cl_m-OCH_3$ (II). Thus, the preferred cases $n = 0$ and $m = 0$ or 1 may be represented by the formulae:

Step 1

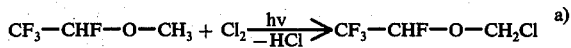

Step 2

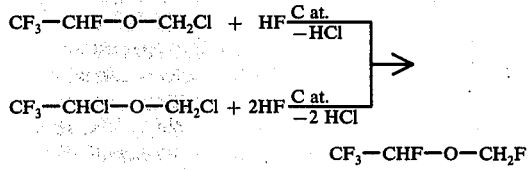

The starting products for the process of preparing $CH_3-CHF-O-CH_2F$ (I), which have the general formula $CF_{3-n}Cl_n-CHF_{1-m}-Cl_m-O-CH_3$ (II), $n$ and $m$ having the meanings given above, may be prepared by substitution of the free OH—group of methyl semiacetals of the perhalogeno-acetaldehydes $CCl_3CHO$, $CCl_2F-CHO$, $CClF_2-CHO$ and preferably $CF_3-CHO$ in the case of $m = 0$ by fluorine, in particular with the aid of (2-chloro-1,1,2-trifluoroethyl)-dialkylamines according to DT-OS 23 40 560, and in the case of $m = 1$ by chlorine with the aid of acid chlorides, preferably phosphorus pentachloride according to DT-OS 23 40 561.

The reaction with chlorine in the process step 1 shall be effected preferably in the $C_1$-group of the ethyl-methyl ether of the formula II. For obtaining the desired selectivity, photochlorination under relatively thermically mild conditions is used. As light sources, there may be used all those conventionally used for this purpose, i.e. those which emit sufficient short wave light for the activation of chlorine, for example light bulbs, ultraviolet lamps, mercury lamps or even strong sun light. The manner of the irradiation depends on the material of the chlorination vessels used. If light-impermeable vessels that are resistant against chlorine and hydrogen chloride are used, for example from nickel, nickel alloys, steel, steel alloys, porcelain or ceramics, the irradiation is effected, for example by an immersed lamp, or if light permeable material of the vessel is used, irradiation from outside is generally used.

As further measures for increasing the selectivity of the photochlorinations described by the above equations, there may be mentioned the draw off of the reaction heat by external cooling, the fine distribution of the stream of chlorine by the use of an introduction device with a frit, stirring of the liquid phase of the ethyl-methyl ether of the formula II to be chlorinated and/or the addition of an inert solvent which is inert towards chlorine and hydrogen chloride, for example $CCl_4$, and the dilution of the chlorine stream with inert gases, for example with hydrogen chloride. They may be applied singly or in any other possible combination.

The preferred embodiment of the reaction step 1 consists in the introduction of undiluted gaseous chlorine through a frit into the liquid phase of the ethyl-methyl ether of the formula II which is placed, without solvent of diluent, at a selected temperature, in a glass vessel provided with an external cooling device and in the irradiation from the outside with a strong light source.

In the preparation of the 1,2,2,2-tetrahalogenoethyl-chloromethyl ether of the formula III with $m = 0$ (step 1 a) by photochlorination of the starting compounds of the formula II with $m = 0$, the reaction temperature may be in the range of from $-10°$ and $+50°$ C. For technical reasons, a temperature of between $0°$ and $+40°$ C, preferably between $+5°$ and $+20°$ C, is used.

The quantity of chlorine used is kept below the stoichiometrically required equimolar quantity in order to avoid overchlorination, thus preferably below 0.9 mole, in particular between 0.5 and 0.8 mole of chlorine per mole of ether of the formula II. It is also possible to use less than the lower limit of 0.5 mole, as this limit has been chosen for practical considerations concerning the expenditure of the distillation and of the loss due to distillation only.

The corresponding chloro-methyl ether $CF_{3-n}Cl_n-CHF-O-CH_2Cl$ with $n = 0$ to 3 can be isolated from the chlorination product, if necessary or desired after the usual washing and drying operations, by fractional distillation in a good yield and in pure form.

The intermediate products of the formula III with $m = 1$ (step 1 b), the ethers $CF_{3-n}Cl_n-CHCl-O-CH_2Cl$ with $n = 0$ to 3, can be prepared as described for the case $m = 0$ or according to DT-OS 23 44 442.

In step 2 of process A, the chloromethyl ethers of the general formula III are preferably fluorinated with hydrogen fluoride in the presence of a fluorination catalyst, in particular according to one of the known processes of gas phase fluorination over a solid bed catalyst, for example aluminium fluoride, or, preferably, chromium oxyfluoride, according to the so-called antimony process (antimony-(V) chlorofluoride + HF), in which the antimony can be replaced in known manner by arsenic, or by reaction with a known fluorination agent, for example SbF$_5$.

The reaction temperature in the preferred catalyzed gas phase process using hydrogen fluoride is limited at the lower end by the temperature at which the catalyst becomes active and at the upper end by the decomposition temperature of the ethers of the formula III to be fluorinated and of the 1,2,2,2-tetrafluoroethyl-fluoromethyl ether (I) on the surface of the catalyst. It is suitable to maintain a fluorination temperature of between 80° and 220° C, preferably between 100° and 170° C, in particular between 120° and 150° C.

The quantity of hydrogen fluoride used in the gas phase process per mole of $CF_{3-n}Cl_n$—$CHF_{1-m}Cl_m$—O—$CH_2Cl$ (III) is at least $(1 + m + n)$ mole. However, in order to complete the reaction, to accelerate it and to evaporate more easily the ethers of the formula II, an excess of HF of up to 10 $(l + m + n)$ mole, preferably between 3 $(l + m + n)$ and 7 $(l + m + n)$ mole, is used.

The 1,2,2,2-tetrafluoroethyl-fluoromethyl ether (I) of the invention is isolated in pure form from the fluorination production, optionally after working up in aqueous phase to remove HF and HCl and drying, by fractional distillation. Isolation of the final product may also be effected with very good success by preparative gas chromatography.

In the reaction steps of the process of the invention in which the reaction is not lead until stoichiometrical reaction rate in order to avoid formation of side-products which are not necessary for the synthesis of (I), the yield of utilizable intermediate products or of $CF_3$—CHF—O—$CH_2F$ can be increased by again subjecting to this reaction the unreacted starting compounds of the respective reaction stage which can be easily separated by fractional distillation.

Under normal conditions, the 1,2,2,2-tetrafluoroethyl-fluoromethyl ether $CF_3$—CHF—O—$CH_2F$ constitutes an easily mobile, colourless and water-clear liquid having a slight but agreeable odor. It is characterized by the following physical properties: boiling point at 760 mm Hg 43° C, molecular weight 150. NMR: doublet of quartets at $\delta = 5.6$ ppm with coupling constants $^2J_{HF} = 57.5$ cycles and $^3J = 2.9$ cycles ($CF_3$—CHF—). 2 Singulets at $\delta = 5.4$ ppm with $^2J_{HF} = 50.1$ cycles and $\delta = 5.5$ ppm with $^2J_{HF} = 54.1$ cycles (—O—$CH_2F$).

The compound is easily miscible with other organic liquids.

When added to the breathing air of humans and air-breathing animals, the 1,2,2,2-tetrafluoroethyl-fluoromethyl ether of the invention has an anesthetizing action. Since it is not inflammable and, compared with other halogenated ethers, very resistant to the so-called breathing lime (for example, a mixture of barium and calcium hydroxide); it can be used advantageously as inhalation anesthetic. By reason of its relatively low boiling point, it can be admixed easily and in controlled manner to breathing mixtures which assure maintenance of the life during anesthetization by a sufficient concentration of oxygen.

The ether of the invention may also be used together with other inhalation anesthetics, for example laughing gas or diethyl ether, furthermore with other anesthetic and therapeutic auxiliary agents, for example muscle relaxants, barbiturates and plasma expanders, as is often necessary in modern combination anesthetization.

$CF_3$—CHF—O—$CH_2F$ causes only a weak excitation during introduction of anesthesia, leads to a condition of deep anesthesia already at a low concentration and is distinguished by very short recovery times. Its anesthetic index, i.e. the ratio of the toxic concentration to the concentration which is necessary for maintaining satisfactory anesthesia, is 5, so that this compound is a very well manipulable inhalation anesthetic.

The effective amount of the compound of this invention to be employed depends on the level of anesthesia to which the human being or air-breathing animal is to be brought, the rate at which anesthesia is to be induced, and the length of time over which anesthesia is to be maintained. Minor volume precentages, for example about 0.25 to 8 percent, or somewhat more, of the compounds in respirable mixtures containing life-supporting amounts of oxygen can be employed. The amount used should be sufficient to provide a significant anesthetic effect, but not so much as to produce unacceptable deleterious side effects. The person controlling the anesthesia can easily regulate the amount of the ether to be used, starting with a small amount, e.g. about 0.25 percent, and gradually increasing the amount until the desired plane of anesthesia is reached. By then monitoring the physical properties of the human being or air-breathing animal as is the usual procedure, the duration and plane of anesthesia can be readily controlled.

The process for preparing the 1,2,2,2-tetrafluoroethyl-fluoromethyl ether of the invention is illustrated by the following Examples. In these Examples, the intermediate fractions obtained during the distillations have not been taken into consideration.

EXAMPLE 1

Preparation of $CF_3$—CHF—O—$CH_2Cl$ 1945 g (14.8 moles) of 1,2,2,2-tetrafluoroethyl-methyl ether was introduced into a cylindrical chlorination vessel provided with an inlet tube and an intercalated frit as well as with two tubes for a deep temperature cooler and a thermometer, and cooled to a temperature of 10° C. 875 g (12.30 moles) of chlorine were introduced at 9° – 16° C so rapidly under irradiation from the outside with a lamp with 200 Watts as they were consumed. The hydrogen chloride formed was eliminated through the deep temperature cooler (−70° C) and was absorbed in water (11.21 moles). After completion of the chlorination, the reaction product was washed successively with a solution of sodium bisulfite, water and sodium bicarbonate and dried over MgSO$_4$. The dried raw product (2129 g) was subjected to fractional distillation, whereupon besides 662 g of pure starting product $CF_3$—CHF—O—$CH_3$ a fraction of 1079 g of $CF_3$—CHF—O—$CH_2Cl$ with a purity of more than 99.3% was obtained. Boiling point 63° C/754 mm.

$CF_3$—CHF—O—$CH_2Cl$. MW 166.5. Calc.: C, 21.6%; H, 1.8%; F, 45.6%; Cl, 21.3%. Found: C, 21.7%; H, 1.8%; F, 45.4%; Cl, 21.3%.

EXAMPLE 2

Preparation of $CF_3$—CHF—O—$CH_2F$ from $CF_3$—CHF—O—$CH_2Cl$ 2872 g (17.26 moles) of 1,2,2,2-tetrafluoroethyl-chloromethyl ether and 2150 g (107.5 moles) of hydrogen fluoride were passed at an internal temperature of 130° – 140° C through a vertically standing reactor from a nickel tube which was electrically heated from the outside and contained a chromium-oxy fluoride catalyst (prepared according to German Patent No. 1,252,182) with a charge volume of 900 ml, within 17 hours, after passage through an evaporator. After leaving the reaction zone, the reaction gases were absorbed in ice water, whereupon the organic product separated as an individual phase, whereas HF and HCl dissolved in water. The organic raw product which had been washed and dried over $MgSO_4$ (2075 g) was then subjected to fractional distillation. A fraction of 1501 g of pure 1,2,2,2-tetrafluoroethyl-fluoromethyl ether, B.p. 42° – 42.5° C/750 mm Hg and $n_D^{20}$ < 1,3000 and 289 g of unreacted $CF_3$—CHF—O—$CH_2$Cl were obtained.

$CF_3$—CHF—O—$CH_2$F. MW 150. Calc.: C, 24.0%; H, 2.0%; F 63.3%. Found: C, 23.8%; H, 2.1%; F 62.8%.

EXAMPLE 3

Preparation of $CF_3$—CHF—O—$CH_2$F from $CF_3$—CHCl—O—$CH_2$Cl

A gaseous mixture of 343 g (1.875 moles) of 1-chloro-2,2,2-trifluoroethyl-chloromethyl ether (prepared according to DT-OS 23 44 442) and 470 g (23.5 moles) of hydrogen fluoride was passed at a temperature of 125° to 135° C within 3 hours through an electrically heated nickel tube reactor which had been filled with a chromium-oxy fluoride catalyst as described in Example 2. The reaction gases leaving the reactor were absorbed in ice-water, whereupon the organic product separated. After washing with water and drying over $MgSO_4$, the product (192 g) was subjected to fractional distillation. In addition to 12 g of starting compound $CF_3$—CHCl—O—$CH_2$Cl, 106 g of $CF_3$—CHF—O—$CH_2$F (B.p. 44° C/765 mm Hg) and 68 g of $CF_3$—CHF—O—$CH_2$Cl (B.p. 63° – 64°0 C/764 mm Hg) were isolated.

We claim:

1. A 1,2,2,2-Tetrafluoroethyl-fluoroethyl ether of the formula $$CF_3\text{—CHF—O—}CH_2F \qquad\qquad I$$

* * * * *